United States Patent [19]

Shiue et al.

[11] 4,436,717
[45] Mar. 13, 1984

[54] $^{18}$F-4-FLUOROANTIPYRINE

[75] Inventors: Chyng-Yann Shiue, Wading River; Alfred P. Wolf, Setauket, both of N.Y.

[73] Assignee: The United States of America as represented by the United States Department of Energy, Washington, D.C.

[21] Appl. No.: 268,422

[22] Filed: May 29, 1981

[51] Int. Cl.$^3$ ...................... A61K 43/00; A61K 49/00
[52] U.S. Cl. ......................................... 424/1.1; 424/9; 548/375
[58] Field of Search ............... 424/1, 1.5, 9; 548/375

[56] References Cited

U.S. PATENT DOCUMENTS

| | | | |
|---|---|---|---|
| 2,899,443 | 8/1959 | Schulze | 260/310 |
| 3,006,759 | 10/1981 | Lorin et al. | 96/55 |
| 3,632,818 | 1/1972 | Allais et al. | 260/310 A |
| 3,646,058 | 2/1972 | Bertin et al. | 260/310 A |
| 3,988,430 | 10/1976 | Dixon et al. | 424/1.5 |

OTHER PUBLICATIONS

Robbins et al., J. Nucl. Med., 19:1346–1352, (1978).
Airey et al., Anales De Quimica, 70; 871–875, (1974).
Robbins, J. Heterocyclic Chem., 14:1107–1108, (1977).
Shiue et al., J. Nucl. Med., 21:68–69, (1980).
Mantescu et al., Radiopharmaceuticals and Labelled Compounds, vol. 1, IAEA, Vienna, 1973, pp. 395–404.
The Chemistry of Radiopharmaceuticals, Masson publ., 1978, p. 118.
Endelman et al., Chem. Abstracts, vol. 86, 1977, abstract #139925a.

*Primary Examiner*—Christine M. Nucker
*Attorney, Agent, or Firm*—Margaret C. Bogosian; James W. Weinberger; Michael F. Esposito

[57] ABSTRACT

The novel radioactive compound $^{18}$F-4-fluoroantipyrine having high specific activity which can be used in nuclear medicine in diagnostic applications, prepared by the direct fluorination of antipyrine in acetic acid with radioactive fluorine at room temperature and purifying said radioactive compound by means of gel chromatography with ethyl acetate as eluent is disclosed. The non-radioactive 4-fluoroantipyrine can also be prepared by the direct fluorination of antipyrine in acetic acid with molecular fluorine at room temperature and purified by means of gel chromctography with ethyl acetate eluent.

3 Claims, No Drawings

$^{18}$F-4-FLUOROANTIPYRINE

BACKGROUND OF THE INVENTION

The U.S. Government has rights in this invention pursuant to Contract Number DE-AC02-76CH00016, between the U.S. Department of Energy and Associated Universities, Inc.

The present invention relates to the novel radioactive pharmaceutical $^{18}$F-4-fluoroantipyrine, the $^{18}$F-labeled analog of 4-fluoro-2,3-dimethyl-1-phenyl-3-pyrazoline-5-one (4-fluoroantipyrine); and to a new method for preparing 4-fluoroantipyrine and said $^{18}$F-labeled analog thereof by the direct fluorination of antipyrine with molecular fluorine ($F_2$) and radioactive fluorine ($^{18}$F) respectively followed by purification by means of gel chromatography.

The prior art discloses radioisotopically labeled antipyrine, particularly labeled with tritium ($^3$H), carbon 14 ($^{14}$C) or with iodine 125 ($^{125}$I) useful in radioimmunoassay to identify individuals of special risk to lung cancer as described in U.S. Pat. No. 3,988,430. The prior art also discloses the direct halogenation of the 1-phenyl group in 3-amino-5-pyrazolones with molecular bromine or chlorine in the presence of acetic acid as disclosed in U.S. Pat. No. 2,899,443; and the preparation of 3-amino-4,4-dihalo-5-pyrazolones by chlorinating or brominating with chlorine or bromine in an inert organic solvent such as carbon tetrachloride, carbon sulfide, acetic acid or chloroform as disclosed in U.S. Pat. No. 3,646,058 and U.S. Pat. No. 3,632,818; and U.S. Pat. No. 3,006,750 discloses a halogenated 1-phenyl-4-chloro- or bromo-5 pyrazolone as a magenta-forming coupler in color photography. However, there is no disclosure of the synthesis of 4-fluoroantipyrine or the radioactive $^{18}$F-labeled analog by the direct fluorination of antipyrine with molecular fluorine or radioactive fluorine.

Labeling of biologically active compounds with positron emitting nuclides where the labeling nuclides are non-active or are introduced in minimally bioactive positions so as not to significantly alter the biochemical characteristics of the compounds, has become especially attractive with the advent of the new positron emission tomographs. The transport to and localization of these compounds in a particular organ can serve as a probe for metabolism in vivo. Antipyrine, a lipophilic compound, has been shown to have high uptake by the brain and has been used to estimate the water content of an organ or of the whole body. Its radioactive analog, $^{14}$C-antipyrine has been investigated as a tracer for estimating regional cerebral blood flow using autoradiography in animals. However, its uptake by cerebral tissues has been shown to be by diffusion and its flow limited, thereby limiting its usefulness as a tracer. 4-Iodoantipyrine, because of its higher partition coefficient, has been shown to be a satisfactory non-volatile tracer for the measurement of regional cerebral blood flow and iodoantipyrine has been used for this purpose in animals. Radioiodinated antipyrines ($^{123}$I and $^{131}$I) have been used to study the symmetry of brain perfusion using the gamma camera and single photon tomography. However, there are several disadvantages for radioiodinated 4-iodoantipyrine: (1) it is unstable in vivo and (2) the half-life for radioactive iodine is relatively long (13.1 hrs for $^{123}$I; and 8 days for $^{131}$I). Use of $^{131}$I in particular, results in a high radiation burden to the individual.

Fluorine-18, however, has attractive properties for use in nuclear medicine: (1) it is a position emitter and has a useful half-life (109.8 min), (2) and C—F bond is strong, resulting in stability of the label, and (3) the substitution of fluorine for hydrogen in a biologically active compound frequently does not alter the biological characteristics of the parent compound. Indeed, several $^{18}$F-labeled compounds have been proven to be effective radiopharmaceuticals. $^{18}$F-2-deoxy-2-fluoro-D-glucose and $^{18}$F-3-deoxy-3-fluoro-D-glucose have been used in brain or heart scanning.

Recently, $^{18}$F-labeled 4'-fluoroantipyrine has been synthesized by a Schiemann reaction, but its ultimate application is limited by its low specific activity (Robbins, et al., J. Nuclear Medicine 19, 1346–1352, 1978). An attempt was made to synthesize 4-fluoroantipyrine by a Schiemann-type reaction starting with 4-aminoantipyrine. The product isolated from this reaction was antipyrylazopyrazopyrazolone instead of the desired 4-fluoroantipyrine (Robbins, J. Heterocyclic Chem. 14, 1107, 1977). 4-Fluoroantipyrine, however, has been synthesized by the electrophilic fluorination of antipyrine with fluoroxytrifluoromethane (Airey, Barton and Ganguly, et al., An. Quin 70, 871, 1974). This method, however, is not suitable for the synthesis of high specific activity $^{18}$F-labeled 4-fluoroantipyrine.

SUMMARY OF THE INVENTION

One object of this invention is to produce the novel radiopharmaceutical $^{18}$F-labeled 4-fluoroantipyrine of high specific activity (radioactivity-mCi/mM), suitable for medical diagnostic applications. More specifically, this novel radiopharmaceutical can be used as a diagnostic agent in the measurement of regional cerebral blood flow.

Another object of this invention is the synthesis of $^{18}$F-4-fluoroantipyrine by direct fluorination.

Additional objects, advantages and novel features of the invention will become apparent from the description given herein and the appended claims.

DESCRIPTION OF THE INVENTION

To achieve the foregoing and other objects and in accordance with the purpose of the present invention, the novel radiopharmaceutical $^{18}$F-4-fluoroantipyrine of high specific activity can be rapidly synthesized by a novel method which comprises the direct fluorination of antipyrine dissolved in acetic acid with $^{18}$F-$F_2$ at room temperature and then purifying the resulting $^{18}$F-4-fluoroantipyrine by means of silica or alumina gel chromatography, using a solvent such as ethyl acetate as the eluent. The silica or alumina columns remove other reaction products and unreacted antipyrine.

This novel radioactive compound, $^{18}$F-4-fluoroantipyrine, has utility as a pharmaceutical in nuclear medicine, as a diagnostic tool, particularly in the measurement of regional cerebral blood flow.

More specifically, this invention also relates to a method of preparing $^{18}$F-4-fluoroantipyrine by direct fluorination of antipyrine. This is accomplished by treating antipyrine in acetic acid, preferably glacial acetic acid, with radioactive fluorine ($^{18}$F), preferably with about 1–2 mole equivalents of $^{18}$F, in a carrier of molecular fluorine ($^{18}$F-$F_2$), preferably 0.1% $F_2$ carrier, at room temperature, and purifying the resulting radioactive $^{18}$F-4-fluoroantipyrine by means of gel chromatography, preferably through silica gel columns with ethyl acetate as eluent. The fluorination reaction is performed by first dissolving antipyrine in a suitable organic solvent, preferably acetic acid, most preferably glacial acetic acid. The fluorination of antipyrine is conducted at room temperature because higher temperatures will complicate the reaction and lower temperatures will freeze glacial acetic acid.

The non-radioactive 4-fluoroantipyrine is similarly prepared by direct fluorination of antipyrine which comprises treating antipyrine in acetic acid, preferably glacial acetic acid, with molecular fluorine preferably about 1–2 mole equivalents F$_2$, and preferably in admixture with an inert gas such as nitrogen (N$_2$) to make 1.9% F$_2$/N$_2$, at room temperature, and purifying said 4-fluoroantipyrine by means of gel chromatography with ethyl acetate as eluent.

The reaction of antipyrine (1) with molecular fluorine in glacial acetic acid yields the by-product 4,4-difluoro-3-hydroxy-2,3-dimethyl-1-phenylpyrazolidin-5-one (2) the desired product 4-fluoroantipyrine (3) and another by-product, probably 4,4-difluoro-3-methyl-1-phenyl-2-pyrazolin-5-one (4) as shown below.

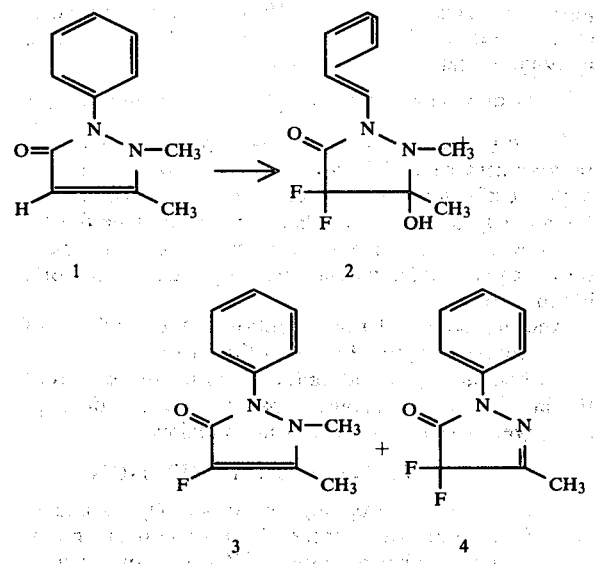

The reaction conditions employed in this fluorination determine the yield ratio of 4-fluoroantipyrine (3) to by-product compound 2. In the presence of excess fluorine, compound 2 beomes the major product. This is presumably due to the addition of fluorine to the compound 3 formed.

The product distribution in the reaction of antipyrine (1) with molecular fluorine at different concentrations was analyzed by gas liquid phase chromatography. The results are set forth in Table 1 below.

TABLE 1

Distribution of Products in the Reaction of Antipyrine with Molecular Fluorine in Glacial Acetic Acid at 25° C. as a Function of [F$_2$]/[Antipyrine]

| [F$_2$]/[Antipyrine] | 0.27 | 0.79 | 1.06 | 1.79 | 4.06 |
|---|---|---|---|---|---|
| % unreacted antipyrine 1 | 88.17 | 62.13 | 48.85 | 18.13 | 6.23 |
| % 4,4-difluoro compound 2 | 1.46 | 9.20 | 14.23 | 33.06 | 49.48 |
| % 4-fluoroantipyrine 3 | 10.20 | 27.44 | 34.00 | 45.24 | 22.43 |

This table clearly shows that the amount of F$_2$ utilized in this reaction determines the amount of 4-fluoroantipyrine produced, the optimum amount being about 2 to 2 moles fluorine per mole antipyrine.

The sequence described above provides a convenient method for the synthesis of 4-fluoroantipyrine and is especially suited for the synthesis of $^{18}$F-labeled 4-fluoroantipyrine of high specific activity wherein antipyrine (1) is fluorinated with $^{18}$F-F$_2$ in lieu of F$_2$, as shown in the following reaction sequence.

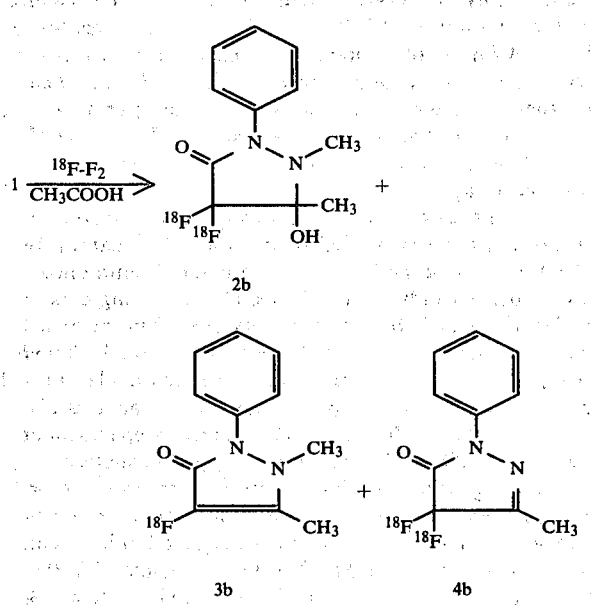

The specific activity of $^{18}$F-4-fluoroantipyrine depends on the specific activity of $^{18}$F-F$_2$, which in turn depends on the total irradiation dose. Typically, 0.44 mCi (Curie units- a measure of radioactivity) of 3b at delivery can be obtained from 4.19 mCi of $^{18}$F-F$_2$ with a specific activity of 0.16 mCi/mg. This method yields 10–15% of $^{18}$F-4-fluoroantipyrine in a synthesis time of 90 minutes from the end of bombardment (EOB). The $^{18}$F-F$_2$ utilized in this synthesis was obtained by the irradiation (bombardment) of a target, consisting of neon containing 0.1% molecular fluorine carrier, with deuterons using the Brookhaven National Laboratory 60" cyclotron.

4-fluoroantipyrine (3) as well as $^{18}$F-4-fluoroantipyrine (3b) can both be purified by separation from the reaction mixture by means of elution with selective solvents through a column of silica gel. Preferably the 4-fluoroantipyrine or the $^{18}$F-4 analog is eluted with ethyl acetate.

The radiopharmaceutical, $^{18}$F-4-fluoroantipyrine has been found particularly useful in diagnostic applications in the measurement of regional cerebral blood flow using emission tomography and generally as an aid in the diagnosis of human cerebrovascular disease.

The following examples are merely illustrative of the invention, and are not to be construed as limiting thereof.

In the following examples melting points were determined on a Fischer-Jones melting points apparatus and were corrected. NMR spectra were measured on a JEOL MH-100 spectrometer and TMS (tetramethylsilane) used as an internal standard. Mass spectra were determined on a Hitachi Perkin-Elmer RMU-7 mass spectrometer. GLPC analysis were carried out on a Hewlett Package 5830A gas chromatograph using a thermal conductivity detector. Radiochemical purities of the products were determined by thin-layer chromatography on silica gel (Eastman) in the following solvent systems: petroleum ether:ethyl ether (1:1 by volume) (A) and ethyl acetate (B).

EXAMPLE 1

Preparation of 4-fluoroantipyrine (4-fluoro-2,3-dimethyl-1-phenyl-3-pyrazolin-5-one) (3)

2.4 mmol of 1.9% $F_2/N_2$ was bubbled into a solution of antipyrine (572 mg, 3.04 mmol) in 30 mL of glacial acetic acid held at room temperature. The light brown solution was then evaporated to dryness. GLPC (10% SE-3 on chromosorb w, 80/100 mesh, 6 ft.×0.125 in. column 190°, 40 ml He/min) analysis of the residue showed peaks at 1.33, 2.42, 6.99, and 8.93 min in the area ratio of 0.96:9.7:31.72:57.67. The first peak is probably 4,4-difluoro-3-methyl-1-phenyl-2-pyrazolin-5-one (4). The other peaks corresponded to 4,4-difluoro-3-hydroxy-2,3-dimethyl-1-phenylpyrazolidin-5-one (2), 4-fluoroantipyrine (3), and antipyrine (1), respectively. The residue was then dissolved in a small amount of ethyl acetate and passed through a silica gel column. The column was eluted with ethyl acetate and fractionated by means of chromatography to give 4,4-difluoro-3-hydroxy-2,3-dimethyl-1-phenylpyrazolidin-5-one (2) (13.67 mg), m.p. 154°–156° C. (lit. 158.5°–159.5° C.) NMR spectrum ($CDCl_3$) was identical with previously reported values and showed peaks at about 7.4–8.0 (m,5H,Ph), 4.6 (br, 1H,OH), 2.8 (t,J=2 Hz,3H,N—$CH_3$), 1.68 (d,J=3 Hz, 3H,C—$CH_3$); the mass spectrum gave a correct M+ at m/e 242 and M+—$H_2O$ at 224; followed by 4-fluoro-2,3-dimethyl-1-phenyl-3-pyrazolin-5-one (3) (84.92 mg), m.p. 132°–134° C. (lit. 135°–136° C.); NMR ($CDCl_3$) 7.64 (S,5H,Ph), 3.04 (d,J=2 Hz,3H,N—$CH_3$) 2.28 (d,J=2 Hz,3H,C—$CH_3$); M+ 206 and antipyrine (342 mg).

EXAMPLE 2

Preparation of $^{18}F$-4-Fluoroantipyrine (3b)

The target consisting of neon containing 0.1% of fluorine carrier (about 50 μmol) was irradiated with deuterons at the Brookhaven National Laboratory 60" cyclotron. The $^{18}F$-labeled fluorine was produced from the $^{20}Ne(d,\alpha)^{18}F$ nuclear reaction. Typically, for a 3 min irradiation at a beam current of 5 μA, the yield of $^{18}F$-$F_2$ is 4.19 mCi (75.6% recovery). The $^{18}F$-$F_2$ was slowly purged from the target chamber into the solution of 11.58 mg (61.5 μM) of antipyrine (1) in 5 mL of glacial acetic acid in a reaction vessel held at room temperature. After all the gas had bubbled through, the reaction mixture was transferred to a round bottom flask and evaporated in vacuo to dryness. The residue was dissolved in a small amount of ethyl acetate and passed through a silica gel column (1×12 cm), eluted with ethyl acetate (50 mL) and evaporated to dryness. The residue containing compounds 2b, 3b and possibly 4b was dissolved in solvent (A) and passed through another silica gel column (1×12 cm), eluted with solvent (A) (150 mL) to remove compounds 2b and 4b. Compound 3b which remained on the column was eluted with ethyl acetate (30 mL) and evaporated to dryness to give 2.8 mg (0.44 mCi at the time of delivery) of product (22.1% chemical yield by weight) and 13.7% radiochemical yield (measured by its radioactivity) in a synthesis time of 87 min from EOB. Thin-layer chromatography showed that compound 3b had $R_f$ 0.21 on solvent (A) and $R_f$ 0.71 on solvent (B). The specific activity of $^{18}F$-4-fluoroantipyrine was 56 mCi/mM.

In an alternative method of purification, the reaction mixture was separated by preparative GLPC. The fluorination mixture was first passed through a silica gel column, eluted with ethyl acetate, and evaporated to dryness. The mixture (compounds 2b, 3b, and 4b) was then dissolved in methanol and separated by preparative GLPC (10% SE-30 on chromosorb w, 80/100 mesh, 5 ft.×0.25 in. column, 190° C., 40 ml He/min.). The peak corresponding to $^{18}F$-4-fluoroantipyrine (3b) was collected.

The foregoing description of a preferred embodiment of the invention has been presented for purposes of illustration and description. It is not intended to be exhaustive or to limit the invention to the precise form disclosed. It is intended that the scope of the invention be defined by the claims.

We claim:

1. A method for preparing the novel radioactive compound $^{18}F$-4-fluoroantipyrine which comprises treating antipyrine in glacial acetic acid with radioactive fluorine in a carrier of molecular fluorine, at room temperature, and purifying said compound by means of gel chromatography with ethyl acetate as eluent.

2. The method according to claim 1, wherein about 1–2 mole equivalents of radioactive fluorine is used.

3. In a method using emission tomography for the diagnostic measurement of regional cerebral blood flow, as an aid in the diagnosis of human cerebrovascular disease, the improvement comprising using a diagnostically effective amount of $^{18}F$-4-fluoroantipyrine as the radioactive material to make said measurement.

* * * * *